United States Patent
Crompton, Jr. et al.

(10) Patent No.: US 7,662,151 B2
(45) Date of Patent: Feb. 16, 2010

(54) CONTACT SENSITIVE PROBES

(75) Inventors: Walter Harvey Crompton, Jr., San Mateo, CA (US); Robert Bryan, San Ramon, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 582 days.

(21) Appl. No.: 11/354,523

(22) Filed: Feb. 15, 2006

(65) Prior Publication Data

US 2007/0191830 A1 Aug. 16, 2007

(51) Int. Cl.
*A61B 18/18* (2006.01)

(52) U.S. Cl. ............................ 606/41; 607/99; 607/122

(58) Field of Classification Search .................. 606/41, 606/42, 45–47
See application file for complete search history.

(56) References Cited

U.S. PATENT DOCUMENTS

| | | | |
|---|---|---|---|
| 4,898,169 A | 2/1990 | Norman et al. | |
| 5,255,679 A | 10/1993 | Imran | |
| 5,339,799 A | 8/1994 | Kami | |
| 6,013,052 A | 1/2000 | Durman et al. | |
| 6,142,994 A | 11/2000 | Swanson et al. | |
| 6,203,525 B1 | 3/2001 | Whayne et al. | |
| 6,214,002 B1 | 4/2001 | Fleischman et al. | |
| 6,241,724 B1 * | 6/2001 | Fleischman et al. | 606/41 |
| 6,241,754 B1 | 6/2001 | Swanson et al. | |
| 6,287,301 B1 | 9/2001 | Thompson et al. | |
| 6,468,272 B1 | 10/2002 | Koblish et al. | |
| 6,511,478 B1 | 1/2003 | Burnside et al. | |
| 6,645,200 B1 | 11/2003 | Koblish et al. | |
| 6,925,318 B2 | 8/2005 | Bencini | |
| 2002/0123749 A1 | 9/2002 | Jain | |
| 2003/0229344 A1 | 12/2003 | Dycus et al. | |
| 2005/0234446 A1 | 10/2005 | Van Wyk et al. | |
| 2007/0191829 A1 | 8/2007 | McGee et al. | |

FOREIGN PATENT DOCUMENTS

| | | |
|---|---|---|
| DE | 4213426 A1 | 10/1992 |
| EP | 1169974 A1 | 1/2002 |
| WO | WO-92/14514 A1 | 9/1992 |
| WO | WO-95/10978 A1 | 4/1995 |
| WO | WO-03/082134 A1 | 10/2003 |
| WO | WO-2004/010883 | 2/2004 |

OTHER PUBLICATIONS

PCT International Search Report dated Jun. 8, 2007 for Int. App. No. PCT/US2007/061820.
Office Action dated Oct. 3, 2008, in U.S. Appl. No. 11/354,481.
Office Action dated Nov. 13, 2008, in U.S. Appl. No. 11/354,481.
Office Action dated May 29, 2009, in U.S. Appl. No. 11/354,481.
Office Action dated Sep. 17, 2008, in U.S. Appl. No. 11/354,481.

* cited by examiner

*Primary Examiner*—Roy D Gibson
(74) *Attorney, Agent, or Firm*—Henricks, Slavin & Holmes LLP

(57) ABSTRACT

Probes that are sensitive to electrode/tissue contact and that are configured to connect an electrode to a power supply and/or provide an indication when the desired level of electrode/tissue contact has been achieved.

13 Claims, 9 Drawing Sheets

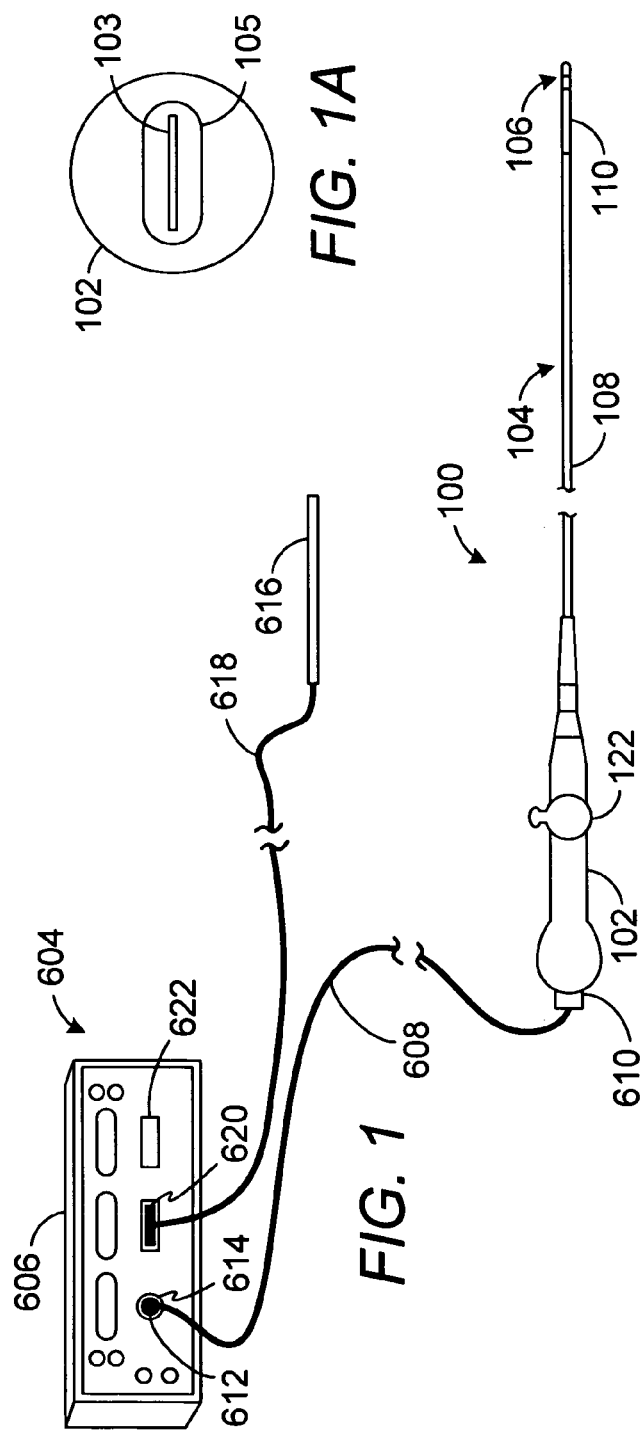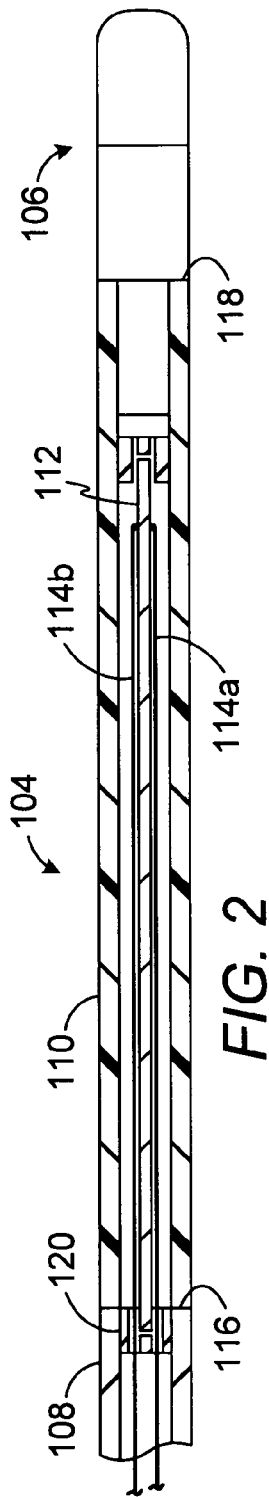

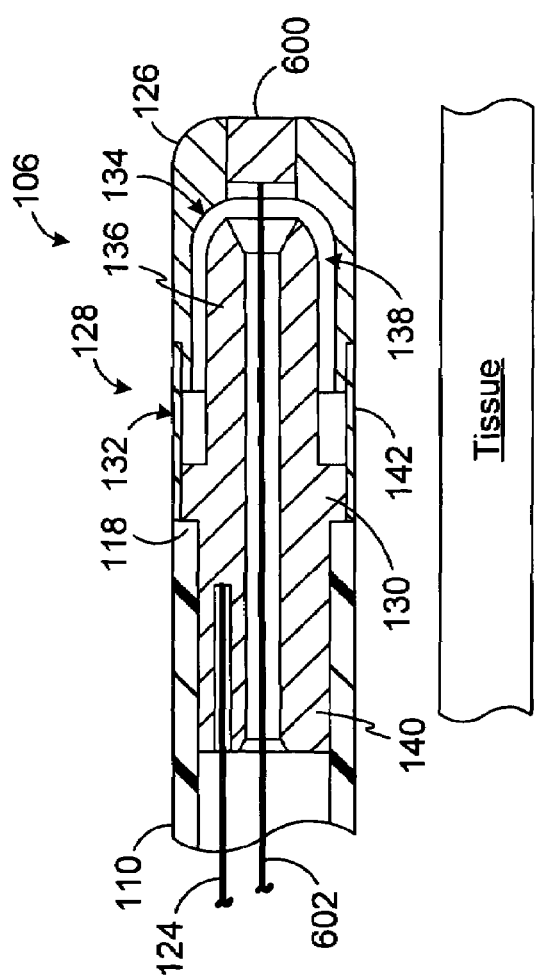
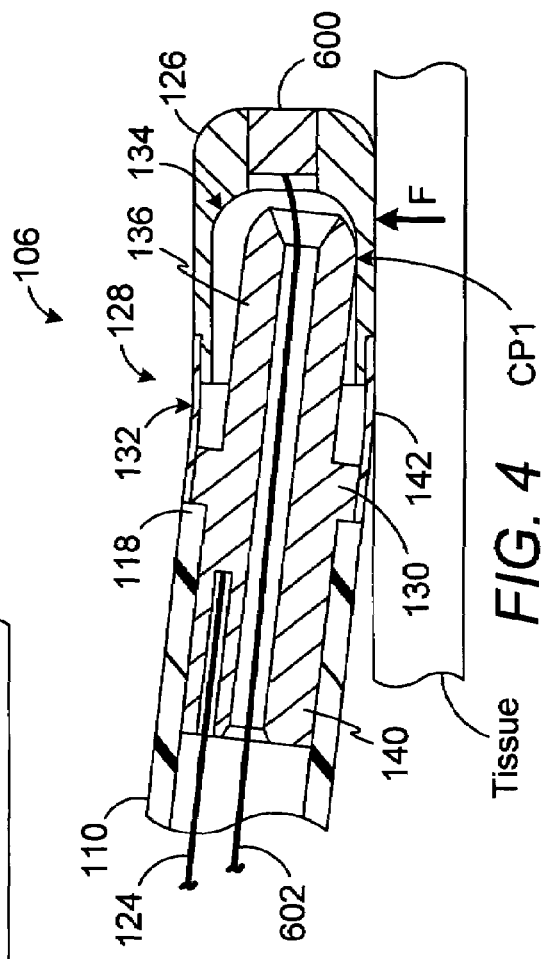
FIG. 3
FIG. 4

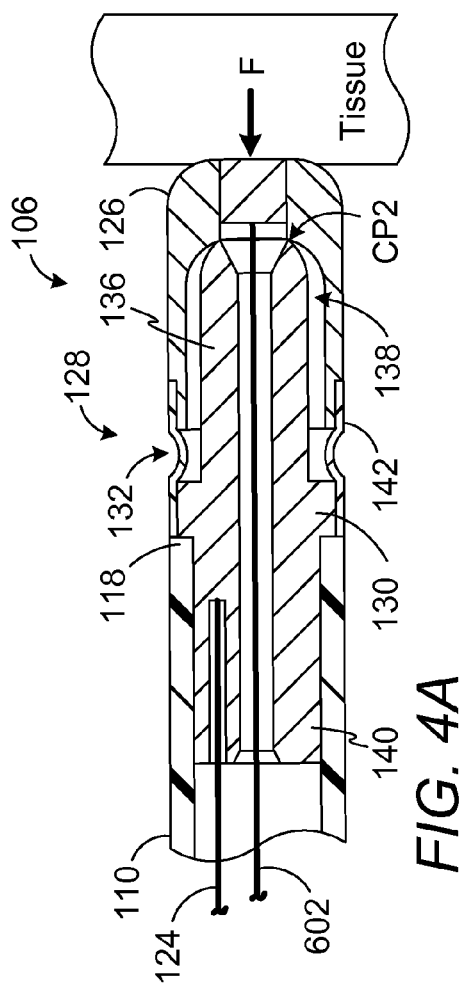
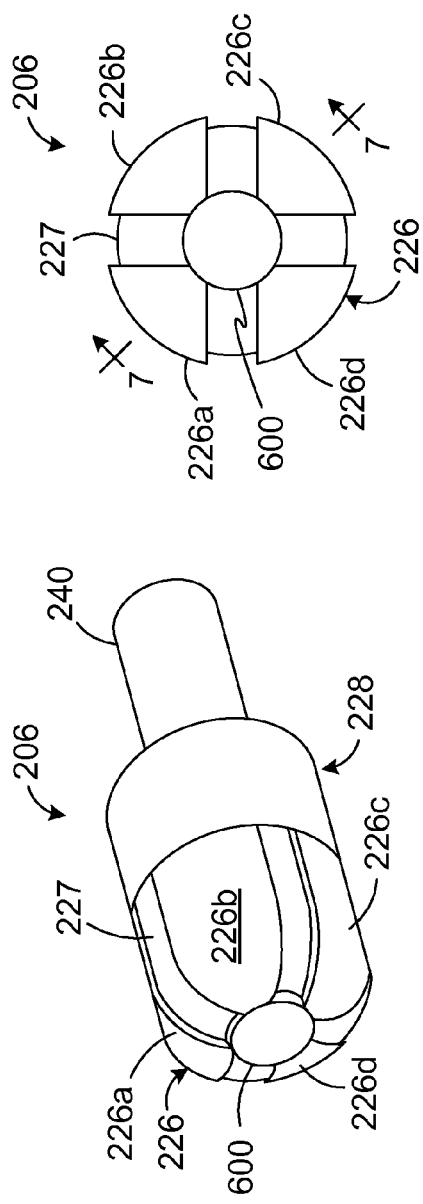
FIG. 4A
FIG. 5
FIG. 6

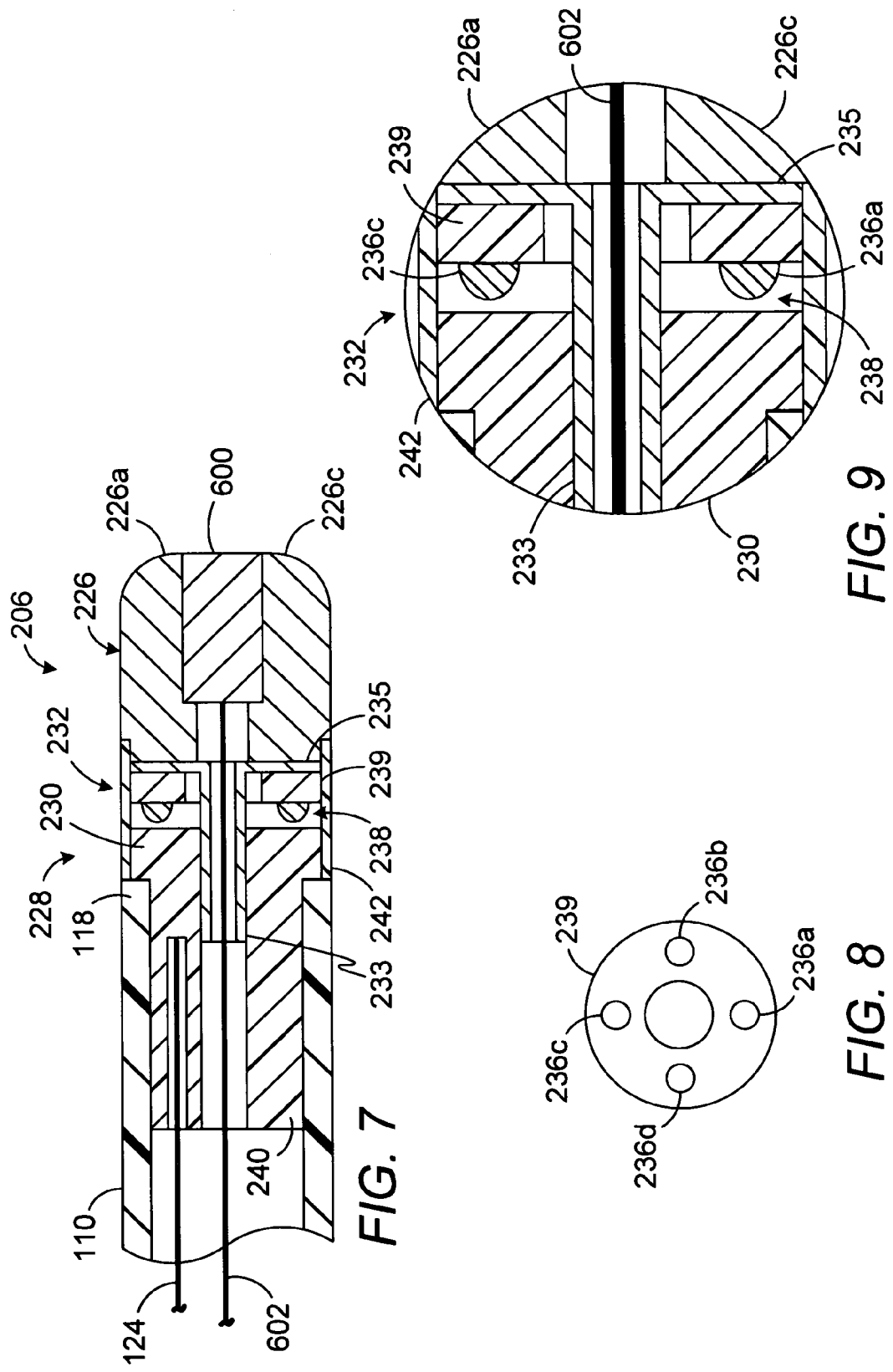

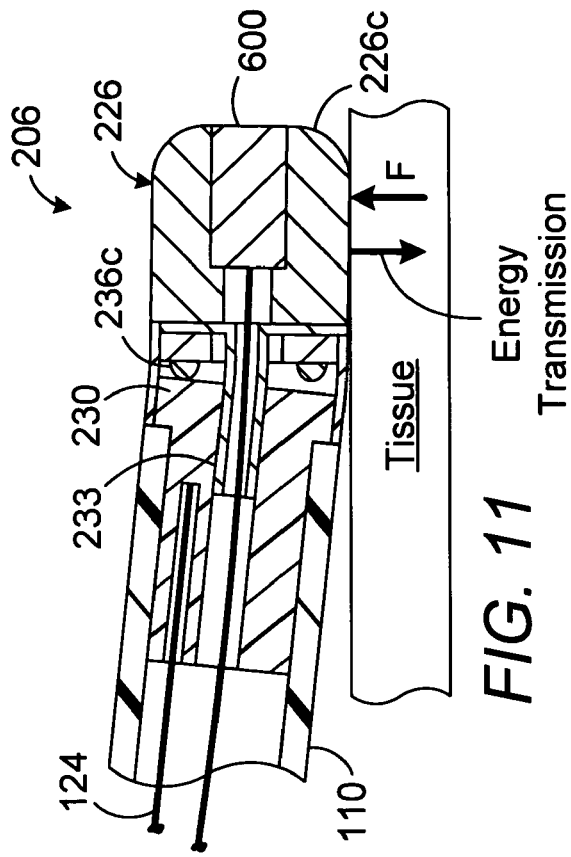
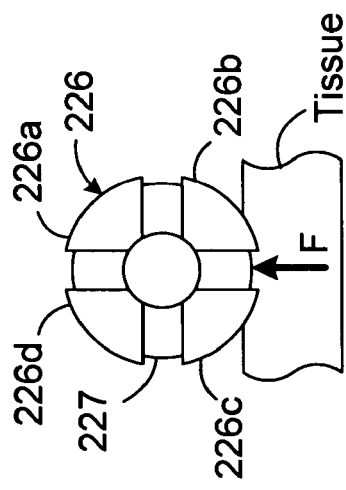
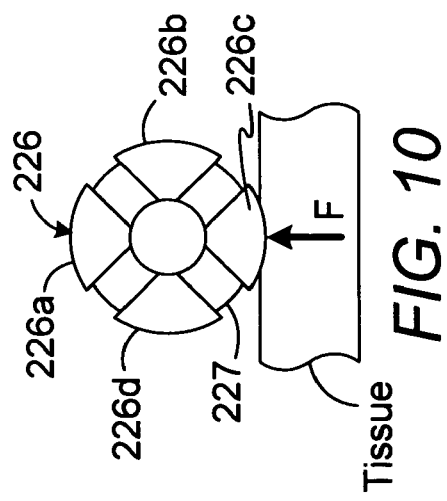
FIG. 11
FIG. 12
FIG. 10

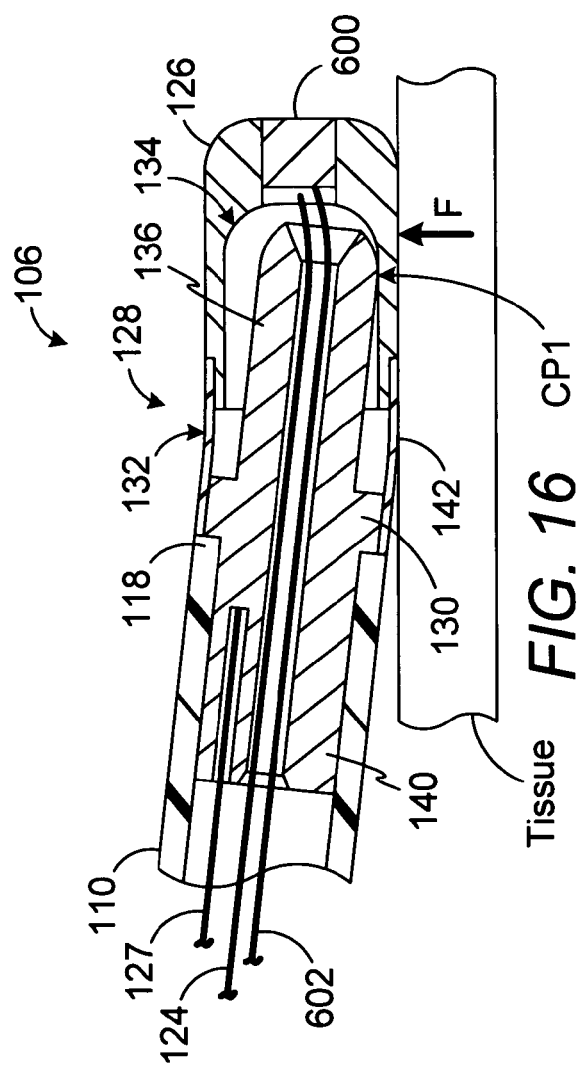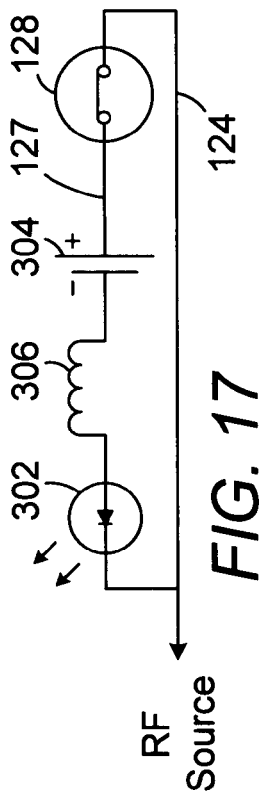

CONTACT SENSITIVE PROBES

BACKGROUND OF THE INVENTIONS

1. Field of Inventions

The present invention relates generally to medical devices that support one or more therapeutic elements in contact with body tissue.

2. Description of the Related Art

There are many instances where therapeutic elements must be inserted into the body. For example, therapeutic elements may be used to form lesions to treat conditions in the heart, prostate, liver, brain, gall bladder, uterus, breasts, lungs and other solid organs. The application of electromagnetic radio frequency ("RF") energy to heat and eventually kill (i.e. "ablate") tissue is one method of forming a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. The tissue coagulation energy is typically supplied and controlled by an electrosurgical unit ("ESU") during the therapeutic procedure. More specifically, after an electrophysiology or electrosurgical device has been connected to the ESU, and one or more electrodes or other energy transmission elements on the device have been positioned adjacent to the target tissue, energy from the ESU is transmitted through the electrodes to the tissue to from a lesion. The amount of power required to coagulate tissue ranges from 5 to 150 W. The energy may be returned by an electrode carried by the therapeutic device, or by an indifferent electrode such as a patch electrode that is secured to the patient's skin.

With respect to the formation of therapeutic lesions in the heart to treat cardiac conditions such as atrial fibrillation, atrial flutter and arrhythmia, some procedures form lesions on the endocardium in order to create a maze for electrical conduction similar to that created by surgical maze procedures. The lesions are carefully placed to interrupt the conduction routes of the most common reentry circuits.

Lesions may be formed by ablating tissue with an electrode that is carried by a probe, such as a catheter or surgical probe. Catheters typically include a relatively long and relatively flexible shaft that carries a distal tip electrode and, in some instances, one or more additional electrodes near the distal end of the catheter. The proximal end of the catheter shaft is connected to a handle which may or may not include steering controls for manipulating the distal portion of the catheter shaft. The length and flexibility of the catheter shaft allow the catheter to be inserted into a main vein or artery (typically the femoral artery), directed into the interior of the heart where the electrodes contact the tissue that is to be ablated. Fluoroscopic imaging is used to provide the physician with a visual indication of the location of the catheter. Exemplary catheters are disclosed in U.S. Pat. Nos. 6,013,052, 6,203,525, 6,214,002 and 6,241,754.

Surgical soft tissue coagulation probes (or "surgical probes") carry one or more electrodes on relatively short, stiff shafts. These probes may be used in endocardial and epicardial procedures where access to the heart is obtained by way of a thoracostomy, thoracotomy or median sternotomy. Such probes also allow endocardial lesions to be formed as a secondary procedure during a primary open heart surgical procedure such as mitral valve replacement, aortic valve replacement, and coronary artery bypass grafting. Exemplary surgical probes are disclosed in U.S. Pat. Nos. 6,142,994, 6,468,272 and 6,645,200.

The present inventors have determined that proper electrode/tissue contact is important issue, for reasons of efficiency and safety, in both catheter-based and surgical procedures. Poor electrode contact with the target tissue increases the amount of coagulation energy that is transmitted into the surrounding tissue and blood. More specifically, the amount of coagulation energy transmitted to surrounding tissue and blood increases as the proximity to the target tissue decreases. With respect to efficiency, the reduction in the amount of energy that is transmitted to the target tissue reduces the likelihood that a transmural, or otherwise therapeutic, lesion will be formed. Poor electrode/tissue contact can also increase the amount of time that it takes to complete the procedure. Turning to safety, transmission of excessive amounts of energy into the surrounding tissue can result in the formation of lesions in non-target tissue which, in the exemplary context of the treatment of cardiac conditions, can impair heart function. The transmission of excessive amounts of energy into the blood can result in the formation of coagulum and emboli. It also increases the amount of energy that is returned by the patch electrode, which can result in skin burns.

SUMMARY OF THE INVENTIONS

An electrode structure in accordance with one embodiment of a present invention includes a base, an electrode, and a joint that secures the electrode relative to the base. The joint may be movable between a first position where the base and electrode are electrically disconnected and a second position where the base and electrode are electrically connected.

A probe in accordance with one embodiment of a present invention includes a probe shaft, an electrode carried by the distal end of the probe shaft, a power wire, and a switch. The switch may be adapted to electrically disconnect the electrode from the power wire when the electrode is in a first position relative to the distal end of the probe shaft and to electrically connect the electrode to the power wire when the electrode is in a second position relative to the distal end of the probe shaft.

A probe in accordance with one embodiment of a present invention includes a probe shaft, an electrode carried by the distal end of the probe shaft, a power wire, and means for electrically connecting the electrode to the power wire in response to the application of a predetermined force to the electrode.

Such electrode structures and probes provide a number of advantages over conventional apparatus. For example, such electrode structures and probes may be used to prevent energy transmission from the electrode unless the proper level of electrode/tissue contact has been achieved. Such electrode structures and probes may also be used to automatically enable energy transmission from the electrode after the proper level of electrode/tissue contact has been achieved.

A probe in accordance with one embodiment of a present invention includes a probe shaft, an electrode, an indicator and means for actuating the indicator in response to the application of a predetermined force to the electrode.

A probe in accordance with one embodiment of a present invention includes a probe shaft, a power wire and a return wire extending though the probe shaft, and an electrode structure having a base connected to the return wire, an electrode connected to the power wire, and a joint that selectively electrically connects the electrode and the base.

A probe in accordance with one embodiment of a present invention includes a probe shaft, an electrode, an indicator, and a strain gauge associated with the distal end of the probe shaft and operably connected to the indicator such that the indicator is actuated in response to the application of a predetermined force to the electrode.

Such probes provide a number of advantages over conventional apparatus. For example, such probes may be used to notify the physician when there is, or is not, an adequate level of electrode tissue contact. The physician may then use this information when deciding whether or not to initiate, continue or discontinue the transmission of energy to tissue.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a perspective view of a tissue coagulation system in accordance with one embodiment of a present invention.

FIG. 1A is an end view of a probe handle in accordance with one embodiment of a present invention.

FIG. 2 is a side, partial section view of the distal portion of a probe in accordance with one embodiment of a present invention.

FIG. 3 is a side, section view of an electrode structure with a switch in a disconnected state in accordance with one embodiment of a present invention.

FIG. 4 is a side, section view of the electrode structure illustrated in FIG. 3 with the switch in a connected state.

FIG. 4A is another side, section view of the electrode structure illustrated in FIG. 3 with the switch in a connected state.

FIG. 5 is a perspective view of an electrode structure in accordance with one embodiment of a present invention.

FIG. 6 is an end view of the electrode structure illustrated in FIG. 5.

FIG. 7 is a section view, taken along line 7-7 in FIG. 6, of the electrode structure illustrated in FIG. 5 with the switch in a disconnected state.

FIG. 8 is a plan view of a portion of the electrode structure illustrated in FIG. 5.

FIG. 9 is an enlarged view of a portion of FIG. 7.

FIG. 10 is an end view of the electrode structure illustrated in FIG. 5 in contact with tissue.

FIG. 11 is a side, section view of the electrode structure illustrated in FIG. 5 with the switch in a connected state.

FIG. 12 is another end view of the electrode structure illustrated in FIG. 5 in contact with tissue.

FIG. 16 is a side, section view of the electrode structure illustrated in FIG. 14 with the switch in a connected state.

FIG. 17 is a circuit diagram showing one aspect of the probe and electrode structure illustrated in FIGS. 13 and 16.

DETAILED DESCRIPTION OF THE PREFERRED EMBODIMENTS

Figure 13:
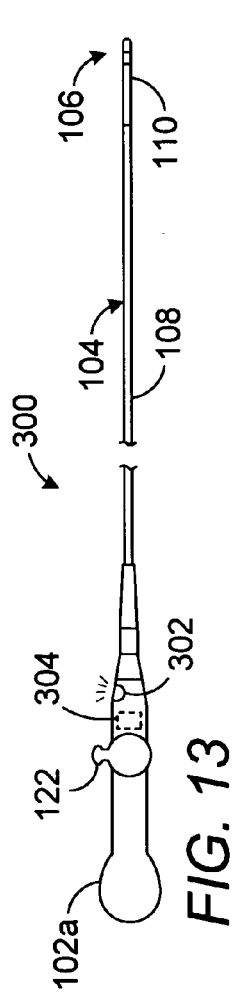
FIG. 13 is a side view of a probe in accordance with one embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
I. Introduction
II. Exemplary Probes With Contact Sensitive Switches
III. Exemplary Probes With Contact Sensitive Indicators
IV. Power Supply and Control The section titles and overall organization of the present detailed description are for the purpose of convenience only and are not intended to limit the present inventions.

I. Introduction

The present inventions may be used within body lumens, chambers or cavities for therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, breasts, uterus, and other regions of the body.

Additionally, although the present inventions are discussed below in the context of catheter-based probes, the inventions also have application in the area of surgical probes. Surgical probes in accordance with the present inventions include a handle, a relatively short shaft, an electrode associated with the distal end of the shaft, and one or more of the contact sensitive switches and/or contact sensitive indicators described below in the catheter context. Preferably, the length of the shaft is about 10 cm to 45 cm. The shaft is also preferably relatively stiff. In other words, the shaft is either rigid, malleable, or somewhat flexible. Exemplary surgical probes are disclosed in U.S. Pat. Nos. 6,142,994, 6,468,272 and 6,645,200, which are incorporated herein by reference.

II. Exemplary Probes With Contact Sensitive Switches

As illustrated for example in FIGS. 1 and 2, a catheter-based probe 100 in accordance with one embodiment of a present invention includes a handle 102, a hollow, flexible catheter shaft 104, and an electrode structure 106 which, as is discussed below with reference to FIGS. 3-4A, is contact sensitive and will prevent energy transmission until the desired level of electrode/tissue contact has been achieved and will automatically permit energy transmission while there is adequate electrode/tissue contact. The exemplary catheter shaft 104 is steerable and formed from two tubular parts, or members, both of which are non-conductive. The proximal member 108 is relatively long and is attached to the handle 102, while the distal member 110, which is relatively short, carries the electrode structure 106. The proximal member 108 may be formed from a biocompatible thermoplastic material, such as a Pebax® material (polyether block amide) and stainless steel braid composite or a polyethylene and stainless steel braid composite, which has good torque transmission properties. An elongate guide coil (not shown) may be provided within the proximal member 108. The distal member 110 may be formed from a softer, more flexible biocompatible thermoplastic material such as unbraided Pebax® material, polyethylene, or polyurethane. The proximal and distal members 108 and 110, which are about 6 French to about 8 French in diameter, may be either bonded together with an overlapping thermal bond or adhesively bonded together end to end over a sleeve in what is referred to as a "butt bond."

With respect to steering, the exemplary catheter probe 100 may be provided with a conventional steering center support 112 and steering wires 114a and 114b. The proximal end of the steering center support 112 is secured near the distal end 116 of the proximal member 108, while the distal end of the steering center support 112 is secured near the distal end 118 of the distal member 110. Mounts 120, which also permit passage of various non-steering wires (not shown here and discussed below), may be used to secure the ends of the center support 112. The steering wires 114a and 114b are secured to opposite sides of the steering center support 112 and extend through the catheter shaft 104 to the handle 102, which is also configured for steering. More specifically, the exemplary handle 102 includes a rotatable knob 122 and the steering wires 114a and 114b are operably connected to the rotatable knob. Additional details concerning suitable handles and steering arrangements are disclosed in U.S. Pat. Nos. 6,013,052 and 6,287,301, which are incorporated herein by reference. Nevertheless, it should be noted that the present inventions are not limited to steerable probes or any particular type of steering arrangement in those probes which are steerable.

Turning to FIGS. 3 and 4, the exemplary electrode structure 106 is connected to a power wire 124 and is configured such that it will not transmit energy from the power wire to the tissue unless there is a suitable level of electrode/tissue contact. To that end, the exemplary electrode structure 106 is provided with an electrode 126 and a contact sensitive switch 128 that keeps the electrode disconnected from the power wire 124 until there is a predetermined electrode/tissue contact force (i.e. about 0.5 g to 10 g for endocardial applications and more, or less, in other applications) and performs the function of electrically connecting the electrode to the power wire in response to the application of the predetermined contact force. The contact sensitive switch 128 will also maintain the electrical connection as long as there is sufficient electrode/tissue contact force.

The exemplary switch 128 includes a base 130, which is secured to the distal end 118 of the catheter shaft distal member 110, and a joint 132, which secures the electrode 126 to the base. The electrode 126 and base 130 are also both electrically conductive and, to that end, are may be formed from electrically conducting materials such as silver, platinum, gold, stainless steel or platinum iridium. The electrode 126 includes a hollow interior region 134 and the base 130 includes a connector post 136 that is located within the hollow interior region of the electrode. The electrode interior region 134 and base connector post 136 are sized and positioned such that there is a gap 138 between the two. The gap 138 electrically insulates the electrode 126 from the base 130 and may be filled with air or an electrically non-conductive fluid. The base 130, which is the portion of the electrode structure 106 that is connected to the power wire 124 in the exemplary probe 100, also includes a mounting post 140 that fits into the distal end 118 of the catheter shaft distal member 110 and is secured thereto with adhesive or other suitable instrumentalities. Additionally, although electrodes in accordance with the present inventions are not so limited, the exemplary electrode 126 will typically be about 5 to 10 French in diameter and about 2 to 10 mm in length.

The base 130 in the illustrated embodiment is formed entirely from electrically conductive material and all of its surfaces are electrically conductive. Alternatively, a base may be formed from both electrically conductive and non-conductive materials. Such a base need only be conductive where necessary. For example, the base could be conductive where it is connected to the power wire 124 and on the portion of the connector post that will contact the electrode 126, with a wire or other conductive element between the two.

The joint 132 in the exemplary electrode structure 106 is a tube 142 formed from a flexible, electrically non-conductive material such as thermoplastic or thermoset elastomer (e.g. silicone or a Pebax®/pellethane combination). Alternatively, a baffled (or "accordion-like") tube may be employed in place of the cylindrical tube 142 in order to augment the ability of the joint 132 to respond to axial forces such as those discussed below in the context of FIG. 4A.

The exemplary switch 128 is shown in the open (or electrically disconnected) state to which it is biased in FIG. 3. The joint 132, which is in its unstressed state in FIG. 3, positions the electrode 126 such that the insulating gap 138 within the electrode extends all the way around the base connector post 136 and no portion of the electrode is in contact with the base connector post. As such, the power wire 124 is electrically disconnected from the electrode 126 and energy from the power wire cannot be transmitted to tissue by the electrode.

The application of a predetermined force F to the electrode 126 will cause the switch 128 to move into the closed (or electrically connected) state that is illustrated in FIG. 4. The force F is the result of a suitable level of electrode/tissue contact which may be accomplished by, for example, using the steering capabilities of the probe 100 to urge the electrode 126 against a tissue surface. The force F causes the joint 132 to deflect and the electrode 126 to pivot relative to the base 130 until the inner surface of the electrode comes into contact with base connector post 136 at contact point CP1. This contact electrically connects the power wire 124 to the electrode 126 so that energy may be transmitted to the tissue in contact with the electrode.

The direction of the force F shown in FIG. 4 is perpendicular to the longitudinal axes of the catheter shaft 104 and electrode structure 106. As such, the electrode 126 pivots about an axis that is also perpendicular to the longitudinal axes of the catheter shaft 104 and electrode structure 106. It should be noted, however, that the joint 132 is configured such that it will respond to the predetermined force F regardless of direction. Referring to FIG. 4A, for example, the joint 132 is configured such that an axial force (i.e. a force in the direction of the longitudinal axes of the catheter shaft 104 and electrode structure 106) will also cause the joint 132 to deflect. Instead of pivoting as it does when subjected to a perpendicular force, the electrode 126 will move axially relative to the base 130 until the inner surface of the electrode comes into contact with base connector post 136 at contact point CP2. This contact electrically connects the power wire 124 to the electrode 126 so that energy may be transmitted to the tissue in contact with the electrode.

Another exemplary electrode structure that may be used in a probe such as, for example, a catheter-based probe that includes the handle and catheter shaft illustrated in FIGS. 1 and 2, is generally represented by reference numeral 206 in FIGS. 5-12. Like the electrode structure 106, the electrode structure 206 is connected to the power wire 124 and is configured such that it will not transmit energy from the power wire to tissue unless there is a suitable level of electrode/tissue contact and will automatically transmit energy while there is suitable contact. The exemplary electrode structure 206 also includes an electrode 226 and a contact sensitive switch 228 which is biased such that it keeps the electrode disconnected from the power wire 124 until there is a predetermined electrode/tissue contact force. The electrode structure 206 is, however, also configured to further reduce the amount of energy that is transmitted into the blood or adjacent non-target tissue. To that end, the electrode may include two or more individually actuatable electrode segments that are electrically insulated from one another. In the illustrated embodiment, the electrode 226 includes four individually actuatable electrode segments 226a-d that are electrically insulated from one another by insulating material 227.

As illustrated for example in FIGS. 7-9, the contact sensitive switch 228 includes a base 230, which is secured to the distal end 118 of the catheter shaft distal member 110, and a joint 232 which secures the electrode 226 to the base. The base includes a mounting post 240 that fits into the distal end 118 of the catheter shaft distal member 110 and is secured thereto with adhesive or other suitable instrumentalities. The joint 232 in the exemplary electrode structure 206 consists of a hollow, flexible post 233, an electrode support disc 235, a plurality of electrical contacts 236a-d, an electrically non-conductive contact support disc 239, and a tube 242. The flexible post 233 and electrode support disc 235 are, in the illustrated embodiment, an integral structure formed from a flexible, electrically non-conductive material such as polypropylene. The electrode segments 226a-d, base 230 and electrical contacts 236a-d may be formed from electrically conducting materials such as silver, platinum, gold, stainless steel or platinum iridium. The electrical contacts 236a-d are each connected to a respective one the electrode segments 226a-d by conductors (not shown) that extend through the electrode support disc 235 and contact support disc 239. The electrical contacts 236a-d in the exemplary embodiment are diametrically opposed (i.e. offset by 180°) from the electrode segments 226a-d to which they are connected.

The base 230 in the illustrated embodiment is formed entirely from electrically conductive material all of its surfaces are electrically conductive. Alternatively, as noted above, a base may formed from both electrically conductive and non-conductive materials and be conductive only where necessary. For example, the base could be conductive where it is connected to the power wire 124 and on the surface that will contact the electrical contacts 236a-d, with a wire or other conductive element between the two.

The components of the exemplary switch 228 are sized and positioned such that there is a gap 238 between the electrical contacts 236a-d and the base 230. The gap 238 electrically insulates the electrical contacts 236a-d from the base 230 and may be filled with air or an electrically non-conductive fluid. The electrical contacts 236a-d will remain electrically insulated from the base 230 until the switch 228 closes in response to the achievement of the predetermined contact force between the electrode structure 206 and tissue. Put another way, the switch 228 performs the function of electrically connecting the electrode segments 226a-d to the power wire 124 in response to the application of the predetermined contact force.

As illustrated for example in FIGS. 10 and 11, the application of a predetermined force F to one of the electrode segments (e.g. electrode segment 226c) will cause the switch 228 to move into one of its closed (or electrically connected) states. The force F is the result of a suitable level of electrode/tissue contact which may be accomplished by, for example, using the steering capabilities of the associated probe to urge the electrode segment against a tissue surface. The force F causes the joint 232 to pivot relative to the base 230 until the electrical contact associated with the electrode segment that is in contact with tissue (e.g. electrical contact 236c) comes into contact with base. This contact electrically connects the power wire 124 to the electrical contact and, accordingly, to the associated electrode segment so that energy may be transmitted to the tissue in by way of the electrode segment.

There may also be instances where two of the electrode segments are in contact with the target tissue structure. Turning to FIG. 12, electrode segments 226b and 226c are in contact with tissue and the predetermined force F is being applied thereto. As a result, the joint 232 will pivot relative to the base 230 until the electrical contacts associated with the electrode segments 236b and 236c (e.g. electrical contacts 236b and 236c) come into contact with base. This contact electrically connects the power wire 124 to the electrical contacts 236b and 236c so that energy may be transmitted to the tissue in by way of the electrode segments 226b and 226c.

III. Exemplary Probes With Contact Sensitive Indicators

Probes in accordance with the present inventions may also be configured such that they provide the physician with an indication, such as a visible and/or audible indication, that a suitable level of electrode/tissue contact has been achieved. The tissue/contact indication may be used, as desired, by the physician during a lesion formation procedure.

One example of such a probe is the exemplary catheter-based probe 300 illustrated in FIGS. 13-17. Probe 300 is substantially similar to probe 100 and similar elements are represented by similar reference numerals. Here, however, the handle 102a is provided with a visible indicator 302 (e.g. an LED) and a power source 304 (e.g. a low voltage DC power source) for the indicator. Alternatively, or in addition, an audible indicator may be employed. The relationship between the power wire 124 and the electrode structure 106 is also different than it is in the probe 100. More specifically, the contact sensitive switch 128 is not used to selectively connect the electrode 126 to the power wire 124. The electrode 126 is directly connected to the power wire 124 and, therefore, is connected to the power supply (discussed in section IV below) regardless of level of electrode/tissue contact. The contact sensitive switch 128 is, instead, used to selectively activate the visible indicator 302.

Figure 14:
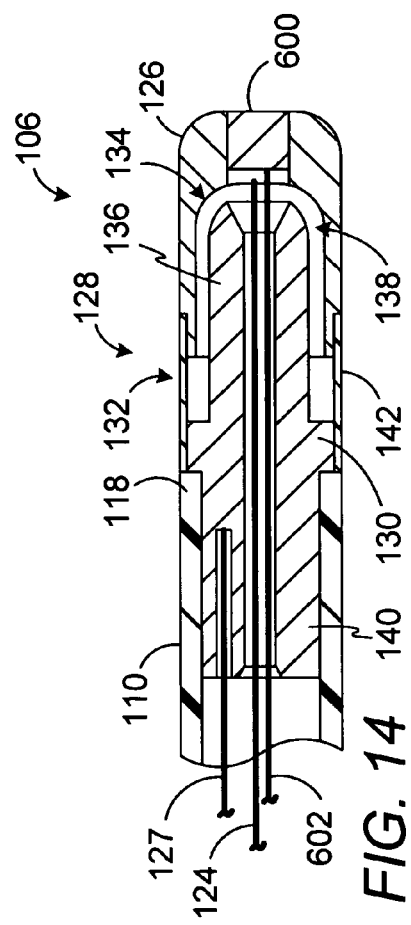
FIG. 14 is a side, section view of an electrode structure with a switch in a disconnected state in accordance with one embodiment of a present invention.
Figure 15:
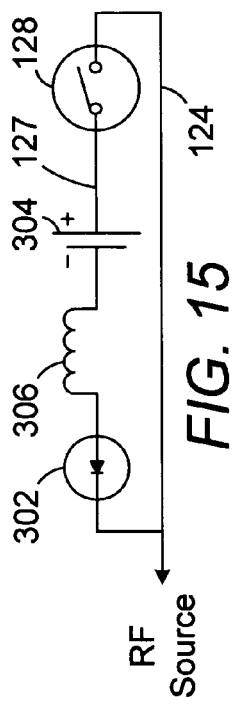
FIG. 15 is a circuit diagram showing one aspect of the probe and electrode structure illustrated in FIGS. 13 and 14.
Figure 18:
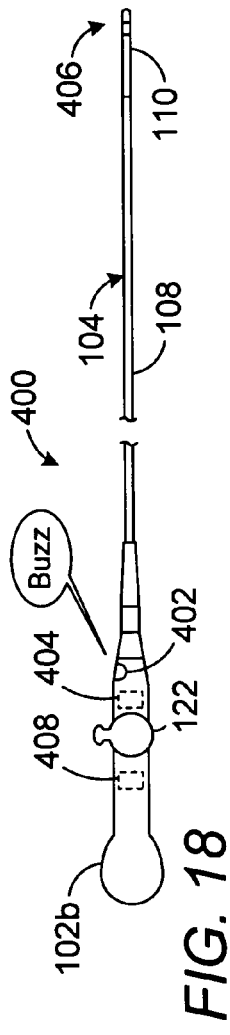
FIG. 18 is a side view of a probe in accordance with one embodiment of a present invention.
Figure 19:
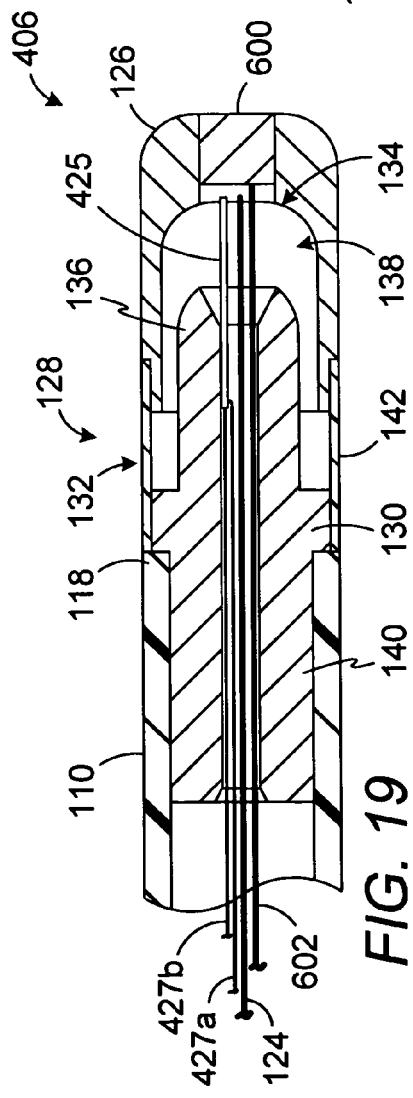
FIG. 19 is a side, section view of an electrode structure in accordance with one embodiment of a present invention.

Referring more specifically to FIGS. 14 and 15, the switch 128 is part of an indicator circuit that includes the visible indicator 302 and power source 304. The circuit also includes the power wire 124, which is connected to the electrode 126, and a return wire 127, which is connected to the base 130 and to the power source 304. An inductor 306 may be used to filter the DC from the RF current that is also transmitted over the power wire 124. When the switch 128 is in the open (or electrically disconnected) state illustrated in FIGS. 14 and 15, the joint 132 positions the electrode 126 such that the gap 138 within the electrode extends all the way around the base connector post 136 and no portion of the electrode is in contact with the base connector post. The return wire 127 is, therefore, electrically disconnected from the electrode 126 and indicator circuit is open. As such, the indicator 302 will be disabled and will not provide an indication (e.g. light) that a suitable level of electrode/tissue contact has been achieved.

Turning to FIGS. 16 and 17, and as discussed above in the context of FIG. 4, the application of a predetermined force F to the electrode 126 will cause the switch 128 to move into the closed (or electrically connected) state. The force F is the result of a suitable level of electrode/tissue contact which may be accomplished by, for example, using the steering capabilities of the probe 300 to urge the electrode 126 against a tissue surface. The force F causes the joint 132 to deflect and the electrode 126 to pivot relative to the base 130 until the inner surface of the electrode comes into contact with base connector post 136 at contact point CP1. Here, this contact connects the return wire 127 to electrode 126 to close indicator circuit. The indicator 302 will, therefore, be enabled and will provide an indication (e.g. light) that a suitable level of electrode/tissue contact has been achieved. The switch 128 will also close when the electrode structure 126 is subjected to axial forces in the manner discussed above in the context of FIG. 4A.

Another exemplary catheter-based probe 400 is illustrated in FIGS. 18-21. Probe 400 is substantially similar to probe 300 and similar elements are represented by similar reference numerals. The power wire 124, for example, is secured directly to the electrode 126. Here, however, the electrode structure 406 includes a strain gauge 425, with signal wires 427a and 427b, that is used to measure the force associated with electrode/tissue contact. The handle 102b is provided with an audible indicator 402 (e.g. a buzzer), a power source 404 for the audible indicator and strain gauge 425, and a controller 408. The controller 408 is connected to the audible indicator 402 and to strain gauge 425. The controller 408 applies a voltage supplied by the power source 404 across the signal wires 427a and 427b to measure resistance at the strain gauge 425. The controller 408 also selectively actuates the audible indicator 402 based on the measured changes in resistance at the strain gauge 425. Alternatively, or in addition, a visible indicator may be employed.

Instead of facilitating electrical connections between various components, the switch 128 is used in the exemplary probe 400 to mount and deflect the strain gauge 425. To that end, the strain gauge 425 is secured to the electrode 126 and to the base connector post 136. The configuration of the strain gauge 425, and the manner in which it is secured to the electrode 126 and base connector post 136, are such that the strain gauge will not be subjected to strain when the joint 132 is in the unstressed state illustrated in FIG. 19. The baseline resistance of the strain gauge 425 is the resistance when it is in the state illustrated in FIG. 19 and the controller 408 will not actuate the audible indicator 402 in response to a baseline resistance measurement.

Figure 21:
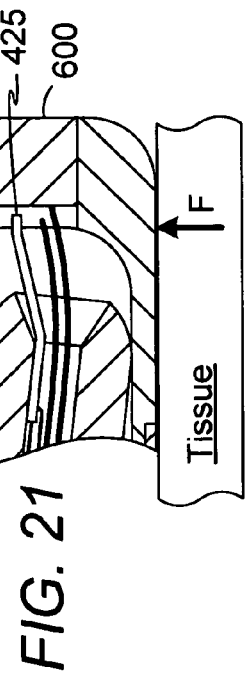
FIG. 21 is side, section view of a portion of the electrode structure illustrated in FIG. 19 with the switch in a connected state.
Figure 20:
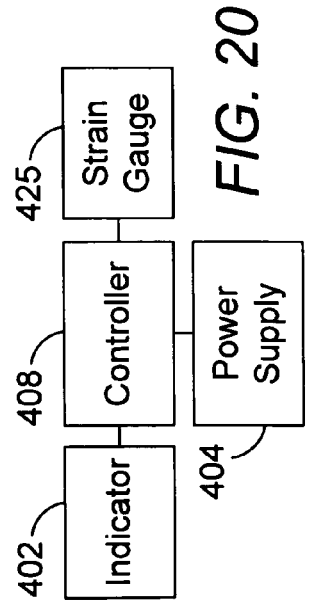
FIG. 20 is a block diagram showing one aspect of the probe and electrode structure illustrated in FIGS. 18 and 19.

The application of a predetermined force F to the electrode 126 will cause the switch 128 to move into the state illustrated in FIG. 21. The force F may be applied by, for example, using the steering capabilities of the probe 400 to urge the electrode 126 against a tissue surface. The force F causes the joint 132 to deflect and the electrode 126 to pivot relative to the base 130. The strain gauge 425 will also deflect and, accordingly, the resistance measured at the strain gauge will change. When the magnitude of the change in resistance from the baseline is indicative of a suitable level of electrode/tissue contact, the controller 408 will actuate the audible indicator 402.

Figure 22:
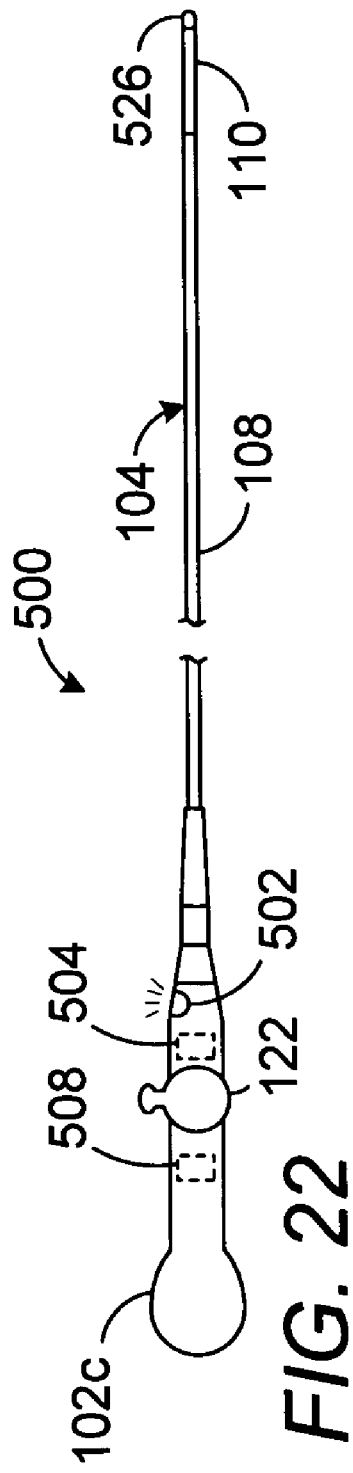
FIG. 22 is a side view of a probe in accordance with one embodiment of a present invention.
Figure 23:
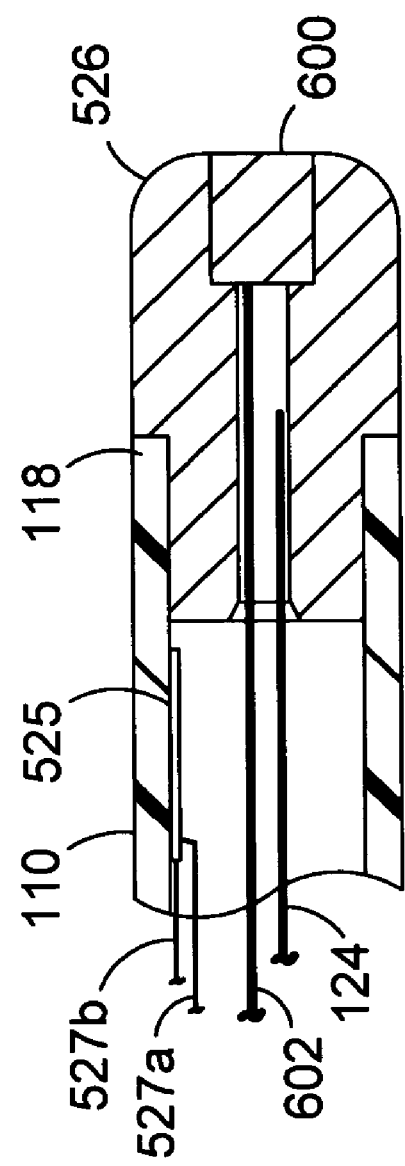
FIG. 23 is a side, section view of the distal portion of the probe illustrated in FIG. 22.

Still another exemplary catheter-based probe is generally represented by reference numeral 500 in FIGS. 22 and 23. Probe 500 is substantially similar to probe 400 and similar elements are represented by similar reference numerals. Probe 500 does not, however, include an electrode structure with an electrode and a switch. Instead, probe 500 includes a conventional tip electrode 526 with a mounting post 540 that fits into the distal end 118 of the catheter shaft distal member 110 and is secured thereto with adhesive or other suitable instrumentalities. The power wire 124 is directly connected to the electrode 526. Probe 500 also includes a strain gauge 525, with signal wires 527a and 527b, that is mounted near the distal end 118 of the catheter shaft distal member 110. The strain gauge 525 is used to measure the force associated with electrode/tissue contact and, to that end, is preferably located as close as practicable to the tip electrode 526.

The handle 102c in the exemplary probe 500 is provided with a visible indicator 502 (e.g. a LED), a power source 504 for the visible indicator and strain gauge 525, and a controller 508. The controller 508 is connected to the visible indicator 502 and to strain gauge 525. The controller 508 applies a voltage supplied by the power source 504 across the signal wires 527a and 527b to measure resistance at the strain gauge 525. The controller 508 also selectively actuates the audible indicator 502 based on the measured changes in resistance at the strain gauge 525. More specifically, the strain gauge 525 will not be subjected to strain when the tip electrode 526 is not in contact with tissue, as is illustrated in FIG. 21. The baseline resistance of the strain gauge 525 is the resistance when it is in the state illustrated in FIG. 21 and the controller 508 will not actuate the visible indicator 502 in response to a baseline resistance measurement.

The application of a force F to the tip electrode 526 will cause the tip electrode to pivot relative to the catheter shaft distal member 110 at the location of the strain gauge 525. The force F may be applied by, for example, using the steering capabilities of the catheter probe 500 to urge the tip electrode 526 against a tissue surface. The strain gauge 525 will deflect and, accordingly, the resistance measured at the strain gauge will change. When the change in resistance from the baseline is indicative of a suitable level of electrode/tissue contact, the controller 508 will actuate the visible indicator 502.

It should also be noted here that probes in accordance with the present inventions may include indicators, such as audible and/or visible indicators, in combination with contact sensitive switches, such as those discussed in Section III, that automatically connect and disconnect power to an electrode based on electrode/tissue contact.

IV. Power Supply and Control

As discussed above, the electrode structures 106, 206, 306 and 406 and electrode 526 are each electrically coupled to a power wire 124 (see, for example, FIG. 3) that conducts coagulating energy. The wire 124 in each of the exemplary embodiments is passed in conventional fashion through a lumen extending through the catheter shaft 104 to an electrical connector 103 (e.g. a PC board, edge card connector, subminiature D connector, ribbon cable connector, or pin and socket connector) in the handle 102-102c which, as illustrated in FIG. 1A, is accessible by way of a port 105.

The electrodes in each of the illustrated embodiments also carry a temperature sensor 600, such as a thermocouple or thermistor. In some embodiments, a reference thermocouple may also be provided. For temperature control purposes, signals from the temperature sensors 600 are transmitted to the source of coagulation energy by way of wires 602 (see, for example, FIG. 3) that are also connected to the aforementioned connectors 103 in the handles.

Turning to FIG. 1, an exemplary electrophysiology system includes the probe 100 (or any of the other aforementioned probes) and a power supply and control apparatus 604. The power supply and control apparatus 604 includes an electrosurgical unit ("ESU") 606 that supplies and controls RF power. A suitable ESU is the Model 4810A ESU sold by Boston Scientific Corporation of Natick, Mass. Power to the probe will typically be controlled as a function of the temperature at the electrodes in order to insure that tissue is coagulated without over-heating and causing coagulum and charring. With respect to temperature sensing at the electrodes, temperature is measured by the aforementioned temperatures sensors. Alternatively, in those instances where temperature sensors are not employed, the respective temperatures at each electrode may be determined by measuring impedance at each electrode.

The ESU 606 transmits energy to the electrodes by way of a cable 608. The cable 608 includes a connector 610, which may be connected to the electrical connector 103, a connector 612, which may be connected to a power output port 614 on the ESU 606. Tissue coagulation energy emitted by the electrodes is returned to the ESU 606 through an indifferent electrode 616 that is externally attached to the skin of the patient with a patch, or one or more electrodes (not shown) that are positioned in the blood pool, and a cable 618. The cable 618 includes a connector 620 that may be connected to one of the power return ports 622 on the ESU 606. Preferably, the ESU power output port 614 and corresponding connector 612 have different configurations than the power return ports 622 and corresponding connector 620 order to prevent improper connections. The amount of power required to coagulate tissue ranges from 5 to 150 w.

Although the present inventions have been described in terms of the preferred embodiments above, numerous modifications and/or additions to the above-described preferred embodiments would be readily apparent to one skilled in the art. By way of example, but not limitation, indicators could be carried on the proximal portion of the probe shaft near the handle (as opposed to on the handle) or on a strain relief device positioned at the distal end of the handle. Some embodiments may include more than one indicator (e.g. an audible indicator and a visible indicator). Moreover, the inventions include any and all combinations of the elements from the various embodiments disclosed in the specification, and systems that comprise a power supply device (such as an ESU) in combination with any of the probes described above and/or claimed below. It is intended that the scope of the present inventions extend to all such modifications and/or additions and that the scope of the present inventions is limited solely by the claims set forth below.

We claim:

1. A probe, comprising:
    a probe shaft defining a distal end;
    an electrode associated with the distal end of the probe shaft;
    a power wire; and
    a switch including
        an electrically conductive base mounted directly onto the distal end of the probe shaft and connected to the power wire, and
        a joint that secures the electrode to the electrically conductive base such that the electrode is movable between a first position where the electrically conductive base and electrode are electrically disconnected from one another and a second position where the electrically conductive base and electrode are electrically connected to one another.

2. A probe as claimed in claim 1, wherein the probe shaft comprises a catheter shaft.

3. A probe as claimed in claim 1, wherein the electrode is pivotable relative to the distal end of the probe shaft.

4. A probe as claimed in claim 1, wherein the electrode includes a plurality of electrically isolated electrically conductive portions.

5. A probe as claimed in claim 4, wherein the switch further includes a plurality of electrical contacts that are respectively connected to the electrically conductive portions and the joint is configured such that the electrical contacts are not in contact with the electrically conductive base when the electrode is in the first position and at least one of the electrical contacts is in contact with the electrically conductive base when the electrode is in the second position.

6. A probe, comprising:
    a probe shaft defining a proximal end and a distal end;
    an electrode carried by the distal end of the probe shaft;
    a sensor wire extending through the probe shaft to the electrode;
    means for conducting tissue coagulation enemy from the proximal end of the probe shaft to the distal end of the probe shaft; and
    means, located adjacent to the distal end of the shaft, for electrically connecting the electrode to the means for conducting tissue coagulation energy in response to the application of a predetermined force to the electrode.

7. A probe as claimed in claim 6, wherein the probe shaft comprises a catheter shaft.

8. A probe as claimed in claim 6, wherein the electrode includes a plurality of electrically isolated electrically conductive portions.

9. A probe as claimed in claim 1, wherein
    the probe shaft defines an inner lumen; and
    the electrically conductive base includes a mounting post that is located within the inner lumen and secured to the probe shaft.

10. A probe as claimed in claim 1, wherein the electrically conductive base includes a connector post contacts the electrode when the electrode is in the second position.

11. A probe as claimed in claim 1, wherein the electrode defines a distal end, the probe further comprising:
    a temperature sensor carried by the distal end of the electrode; and
    a signal wire connected to the temperature sensor.

12. A probe as claimed in claim 11, wherein
    the electrically conductive base defines proximal and distal ends and includes a signal wire lumen that extends from the proximal end to the distal end; and
    the signal wire passes through and extends distally beyond the distal end of the signal wire lumen.

13. A probe as claimed in claim 1, wherein the entire electrode is distal of the entire electrically conductive base.

* * * * *